United States Patent

Horn

[11] Patent Number: 4,848,890
[45] Date of Patent: Jul. 18, 1989

[54] VISOR WITH POINT SUN BLOCKING

[75] Inventor: Michael Horn, South Setauket, N.Y.

[73] Assignee: Grumman Aerospace Corporation, Bethpage, N.Y.

[21] Appl. No.: 90,055

[22] Filed: Aug. 27, 1987

[51] Int. Cl.⁴ ............................. G02C 7/10; G02C 7/02
[52] U.S. Cl. ...................................... 351/44; 351/45; 351/158
[58] Field of Search ..................... 351/158, 41, 44, 45; 350/331 R

[56] References Cited

U.S. PATENT DOCUMENTS

| | | |
|---|---|---|
| 3,167,607 | 1/1965 | Marks . |
| 3,245,315 | 4/1966 | Marks et al. . |
| 3,409,909 | 11/1968 | Scott et al. . |
| 3,943,573 | 3/1976 | Budmiger . |
| 4,021,935 | 5/1977 | Witt . |
| 4,071,912 | 2/1978 | Budmiger . |
| 4,152,846 | 5/1979 | Witt . |
| 4,155,122 | 5/1979 | Budmiger . |
| 4,279,474 | 7/1981 | Belgorod . |
| 4,462,661 | 7/1984 | Witt . |
| 4,482,326 | 11/1984 | Witt . |
| 4,491,390 | 1/1985 | Tong-Shen . |

*Primary Examiner*—Rodney B. Bovernick
*Assistant Examiner*—P. M. Dziezynski
*Attorney, Agent, or Firm*—Pollock, VandeSande & Priddy

[57] ABSTRACT

Eye gear is provided to protect a wearer from irritating direct sunlight. Liquid crystal matrices are positioned over the wearer's eyes and a sun-tracking photosensor and related electronics determines the area of direct sunlight within the viewer's field of view. Segments of the matrix corresponding to the sunlit area are switched to a light-blocking state so that the remaining unaffected field of the view may be maintained.

6 Claims, 2 Drawing Sheets

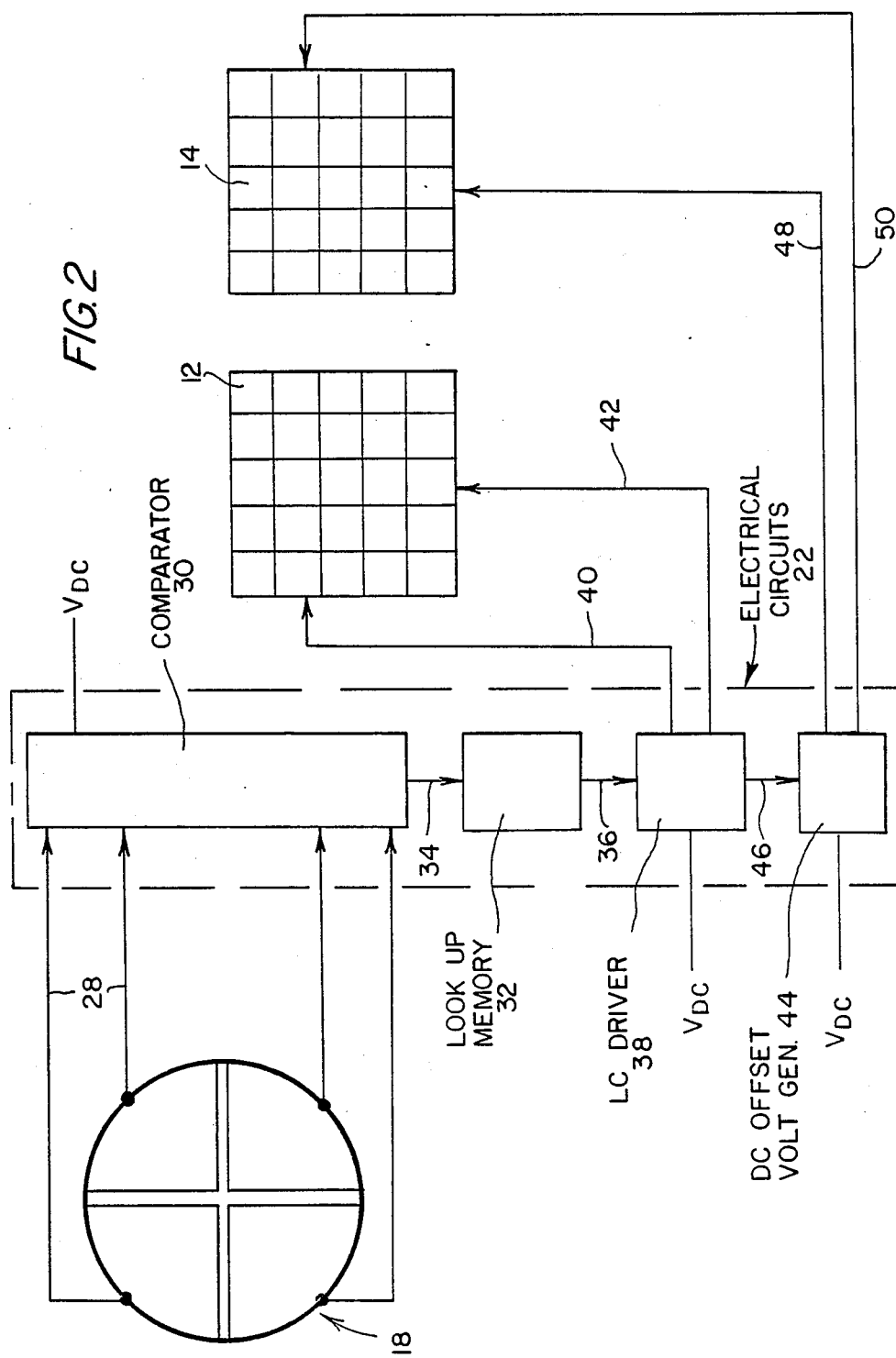

VISOR WITH POINT SUN BLOCKING

FIELD OF THE INVENTION

The present invention relates to protective eye wear, and more particularly to a visor for selectively blocking the sun in an otherwise clear field of view.

BACKGROUND OF THE INVENTION

Pilots and astronauts have long been plagued with maintaining operation of their craft while being "blinded" by the sun. It is common practice to provide protective eye gear, in the form of visors, goggles or sunglasses, which sufficiently filters the sun's light to enable an individual to operate in strong sunlight. Although such devices may satisfactorily filter the sun's rays, they also darken the remaining clear field of view. This presents a dangerous situation for pilots in a combat situation where the entire field of view must be visually monitored on a constant basis without attenuating light from objects such as approaching hostile aircraft.

BRIEF DESCRIPTION OF THE PRESENT INVENTION

The present invention is directed to protective eye wear for pilots, astronauts and others who have a need for blocking or eclipsing the strong light from only that point in the field of vision where the sun shines. With the present invention in place, a pilot would have a relatively clear field of view where he could sight objects in the sky without being impeded by light filters that might otherwise prevent detection of targets and other objects necessary for clear sighting.

The invention utilizes a visor with a liquid crystal (LC) matrix over the surface thereof, individual elements of the matrix being selectively energizable to present light blocking points in a wearer's field of vision corresponding to the instantaneous position of the sun in a field of view. As the field of view changes, and more particularly the position of the sun within the field of view, the light blocking LC elements will change within the matrix to correspond with the shifted sun position. A two-dimensional photosensor mounted on the visor detects changing sun position within the field of view so that corresponding LC elements may be activated to a light blocking condition.

The protection offered by the present invention not only greatly aids pilots and astronauts but is also applicable to industrial and sports applications where similar problems with light "blindness" may temporarily or permanently impede an individual's sight.

BRIEF DESCRIPTION OF THE FIGURES

The above-mentioned objects and advantages of the present invention will be more clearly understood when considered in conjunction with the accompanying drawings, in which:

FIG. 2 is a block diagram indicating the individual components of the present invention.

DETAILED DESCRIPTION OF THE PRESENT INVENTION

Figure 1:
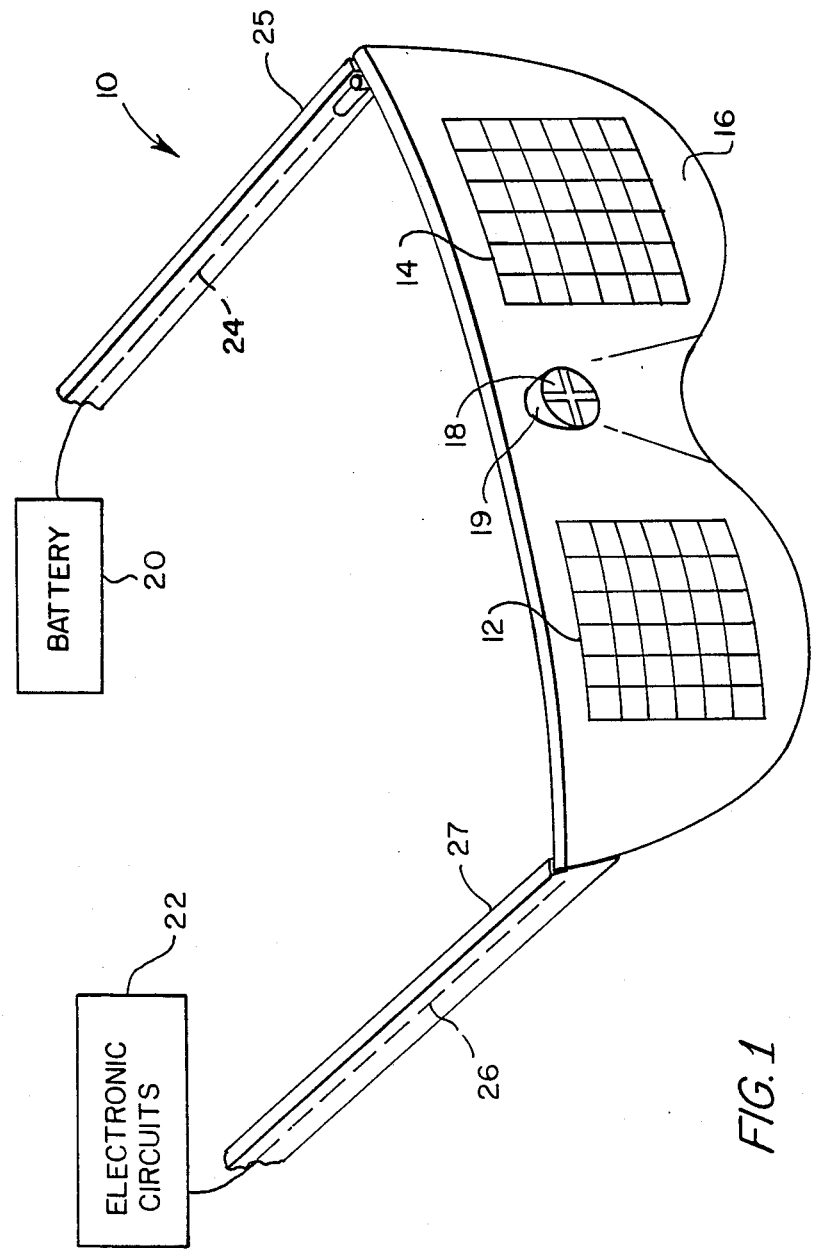
FIG. 1 is a diagrammatic illustration of the present invention illustrating the principal components thereof.

Referring to FIG. 1 reference numeral 10 generally indicates in diagrammatic form a visor or other protective eye wear (goggles, sunglasses, etc.) which is worn by an individual. Two liquid crystal (LC) matrices 12 and 14 are aligned with the wearer's eyes and individual elements of the matrices may be energized, as will be presently explained, to block incident irritating light, such as strong sunlight, in only those areas of a wearer's field of view where the sunlight is present. Other elements of the matrices will remain light transmissive so that the wearer's field of view becomes undisturbed by the irritating light. The visor 16 is merely shown in an illustrative shape and may be suited for a particular application such as aeronautics, avionics, space, sports, recreation, industrial, etc. A sectional photosensor 18 is centered between the LC matrices and serves to track the shift of sunlight within the field of view of the wearer. In an elementary form of the photosensor, it may be a four guadrant photosensor including four individual photodiodes of conventional design and fabrication. A fish eye lens 19 is shown mounted over the photosensor and is intended to focus sunlight or other strong light on the photosensor in a manner corresponding to the appearance of sunlight within a wearer's field of vision. Thus, the combination of photosensor 18 and fish eye lens 19 serves as a sunlight tracking means. The LC matrices and necessary electronic circuits 22 (to be discussed hereinafter) are powered by a battery 20, which may include discrete, solar, integrated rechargeable, or other suitable power supplies. In the event the protective eye gear is to have temples 25, 27, respective wires 24 and 26 may be incorporated in the temples to connect the battery and electronic circuits together with the LC matrices. In a typical situation, conductors (not shown) are incorporated in the visor 16 to connect the matrices 12 and 14 with the wires 24 and 26. This technique is quite conventional in the printed circuit art.

FIG. 2 illustrates in greater detail the circuitry necessary for achieving the purposes of the invention. The electrical circuits indicated by reference numeral 22 in FIG. 1 are shown schematically to include a number of electronic means.

The wiring generally indicated by reference numeral 26 in FIG. 1 is more specifically shown in FIG. 2 to include leads 28 respectively connected to each section of the sun tracking photosensor 18. Although a four quadrant photosensor is shown, a greater number of sections could be employed. Alternately, a charge coupled device (CCD) could be employed with a pixel distribution corresponding to the individual elements of the matrices 12 and 14. This would allow individual pixels of the CCD photosensor to precisely and accurately block out only those LC segments which are necessary to block direct sunlight.

The photosensor leads 28 are connected to the input of comparator 30 which compares the voltage generated by each quadrant in response to an instantaneous incident light condition on the photosensor 18. As will be appreciated, as the photosensor tracks incident sunlight, the voltages from individual quadrants will vary. The output of comparator 30 is connected, via lead 34, to a look-up memory 32 which stores a look-up table that relates, on a two-dimensional basis, the voltage conditions for the four photosensor quadrants as a function of incident sunlight on the photosensor. Thus, as incident sunlight varies its effect on each quadrant of the photosensor, an instantaneous corresponding position of sunlight is calculated relative to the surfaces of the matrices 12 and 14 which will become energized to block sunlight from passing through.

Again, it should be emphasized that, although the description of the invention centers around a four quadrant photosensor, a greater number of elements for a photosensor is anticipated for more accurately blocking only the area of incident sunlight while retaining the remaining field of view clear.

The output of the comparator 30 will generate data corresponding to X-Y coordinates in the matrices 12 and 14 where sunlight blocking areas are to be created. In order to energize individual LC elements to a blocking condition, an LCD driver 38 is connected via lead 36 to the output of memory 32. The driver provides sufficient power for switching individual elements of the LC matrix, as is done in conventional liquid crystal displays. Output leads 40, 42 determine the X-Y coordinates of individual LC elements to be switched to a light blocking condition in matrix 12. However, since parallax normally exists between an individual's left and right eyes, sunlight viewed through the display matrix 12 will appear somewhat offset from the sunlight appearing through matrix 14. In order to create the offset X-Y coordinates in matrix 14, the output from LC driver 38 undergoes DC offset in a conventional adjustable DC offset voltage generator 44 which provides the offset X-Y coordinate values to matrix 14 via leads 48, 50. By adjusting the offset in generator 44, the light blocking area can be aligned in both the left and right eyes of the visor wearer and different parallax corrections for different individuals may be accommodated.

Once an individual has set the DC offset, sun blocking may be effected in both eyes satisfactorily while otherwise maintaining full clear fields of view.

Accordingly, as will be appreciated, the present invention offers the electronic capability of blocking the effects of strong light, such as sunlight, within a field of view. This enables a wearer to comfortably maintain vision of a field of view without shutting one's eyes, squinting or relying on light filters that unnecessarily attenuate the light from the remaining clear field of view.

It should be understood that the invention is not limited to the exact details of construction shown and described herein for obvious modifications will occur to persons skilled in the art.

I claim:

1. Protective eye gear for minimizing the effects of irritating sunlight in a field of view, the eye gear comprising:
    a light-transmissive lens to be positioned over a wearer's eyes;
    a matrix of electrically controlled and normally transparent segments mounted over the lens, individual segments being selectively switched to block direct sunlight from a wearer's field of view;
    photosensor means located in proximity to the lens for tracking the area of direct sunlight relative to a wearer's entire field of view; and
    control means connected between the photosensor means and the matrix segments for selectively switching segments in the matrix to a light-blocking state, the switched segments corresponding to the area of the wearer's field of view where direct sunlight exists;
    wherein segment light blocking is accompanied by a remaining clear field of the view for the wearer;
    the photosensor means including a plurality of individual segments located adjacent one another; and
    a lens mounted over the segments for focussing direct sunlight onto a portion of the segments, corresponding to the location of the direct sunlight within the otherwise clear field of view;
    the control means including
    (a) comparator means having inputs connected to respective photosensor segments for detecting which photosensor segments are receiving direct sunlight;
    (b) memory means connected to the output of the comparator means and containing a look-up table for establishing a unique memory output dependent upon the condition of the photosensor segments at a moment in time and selecting which of the matrix segments are to be switched to a sun-blocking state corresponding to the photosensor segments receiving direct sunlight; and
    (c) driver means connected between the output of the memory means and the matrix segments for switching selected segments between light-blocking and light-transmitting states; and
    (d) means connected between the driver and a second matrix mounted over a second lens for offsetting blocking segments thereof corresponding to blocked segments of the first matrix but corrected for parallax.

2. The structure set forth in claim 1 wherein the matrices are fabricated from liquid crystal segments.

3. The structure set forth in claim 2 wherein the photosensor segments are fabricated from photodiodes.

4. The structure set forth in claim 2 wherein the photosensor segments are fabricated from charge-coupled devices.

5. A method for protecting a person's vision from strong light within a field of view, the method comprising the steps:
    tracking the strong light on a multi-segment photosensor area corresponding to a field of view;
    comparing the states of the photosensor segments with a look-up table for establishing a unique memory output dependent upon the condition of the photosensor segments at a moment in time;
    interposing matrix means between the light and a person's eye;
    selectively switching individual segments of the matrix means to a light-blocking state in response to the memory output corresponding to shifts of incident strong light on the photosensor area while maintaining unaffected matrix segments in a light-transmitting state thereby only blocking the wearer's field of view in the area of strong light exposure.

6. The method set forth in claim 5 together with the step of providing two matrices, one over each of the wearer's eyes; and
    offsetting the blocked segments in one matrix relative to the other for achieving parallax correction.

* * * * *